(12) United States Patent
Wan

(10) Patent No.: US 10,386,185 B2
(45) Date of Patent: Aug. 20, 2019

(54) INFORMATION PROCESSING METHOD AND ELECTRONIC DEVICE

(71) Applicants: Beijing Lenovo Software Ltd., Beijing (CN); Lenovo (Beijing) Co., Ltd., Beijing (CN)

(72) Inventor: Xi Wan, Beijing (CN)

(73) Assignees: Beijing Lenovo Software Ltd., Beijing (CN); Lenovo (Beijing) Co., Ltd., Beijing (CN)

( * ) Notice: Subject to any disclaimer, the term of this patent is extended or adjusted under 35 U.S.C. 154(b) by 1250 days.

(21) Appl. No.: 14/498,236

(22) Filed: Sep. 26, 2014

(65) Prior Publication Data

US 2015/0238136 A1   Aug. 27, 2015

(30) Foreign Application Priority Data

Feb. 21, 2014 (CN) .......................... 2014 1 0060969

(51) Int. Cl.
  *G01C 19/00* (2013.01)
  *A61B 5/11* (2006.01)
  (Continued)

(52) U.S. Cl.
  CPC ............... *G01C 19/00* (2013.01); *A61B 5/11* (2013.01); *G06F 3/014* (2013.01); *G06F 3/017* (2013.01);
  (Continued)

(58) Field of Classification Search
  CPC ........................................................ A61B 5/11
  See application file for complete search history.

(56) References Cited

U.S. PATENT DOCUMENTS 6,965,842 B2   11/2005  Rekimoto
2004/0243342 A1*  12/2004  Rekimoto ............... G06F 3/011
                                               702/150
(Continued)

FOREIGN PATENT DOCUMENTS

CN    1531676 A    9/2004
CN    102624981 A    8/2012
(Continued)

OTHER PUBLICATIONS

First Chinese Office Action regarding Application No. 201410060969.8 dated Jul. 5, 2017. English translation provided by http://globaldossier.uspto.gov.

*Primary Examiner* — John E Breene
*Assistant Examiner* — Jeffrey C Morgan
(74) *Attorney, Agent, or Firm* — Harness, Dickey & Pierce, P.L.C.

(57) ABSTRACT

An information processing method and an electronic device are provided. The method includes: obtaining first parameter information indicating a current posture of a first body part by a first sensor among M sensors of an electronic device fixed on the first body part; judging whether the first parameter information meets a predetermined condition; determining that the current posture of the first body part is a first posture in a case that the first parameter information meets the predetermined condition; obtaining N second parameters by N sensors other than the first sensor among the M sensors, wherein 1≤N<M; and determining a first posture direction that the first body part in the first posture points towards based on the N second parameters.

10 Claims, 4 Drawing Sheets

(51) Int. Cl.
   *G06F 3/01*     (2006.01)
   *G06F 3/0346*   (2013.01)
   *A61B 5/00*     (2006.01)

(52) U.S. Cl.
   CPC ............ *G06F 3/0346* (2013.01); *A61B 5/681* (2013.01); *A61B 2562/0219* (2013.01); *A61B 2562/0247* (2013.01); *A61B 2562/043* (2013.01)

(56) References Cited

U.S. PATENT DOCUMENTS

| | | |
|---|---|---|
| 2012/0209560 A1 | 8/2012 | Young |
| 2013/0207890 A1 | 8/2013 | Young |
| 2014/0349580 A1 | 11/2014 | Chen |
| 2015/0103019 A1 | 4/2015 | Young |
| 2015/0148072 A1* | 5/2015 | Snyder ................. H04W 4/025 455/456.2 |
| 2017/0115632 A1* | 4/2017 | Matsuno .............. G04B 19/048 |
| 2018/0259913 A1* | 9/2018 | Brown .................... G04G 21/02 |

FOREIGN PATENT DOCUMENTS

| | | |
|---|---|---|
| CN | 102741787 A | 10/2012 |
| CN | 103631368 A | 3/2014 |
| EP | 1457863 A2 | 9/2004 |
| WO | WO-2011047438 A1 | 4/2011 |

\* cited by examiner

INFORMATION PROCESSING METHOD AND ELECTRONIC DEVICE

The present application claims the priority to Chinese Patent Application No. 201410060969.8, entitled "INFORMATION PROCESSING METHOD AND ELECTRONIC DEVICE", and filed with the Chinese State Intellectual Property Office on Feb. 21, 2014, the entire disclosure of which is incorporated herein by reference.

BACKGROUND

Technical Field

The present disclosure relates to the field of electronic technology, and in particular to an information processing method and an electronic device.

Related Art

With development of electronic technology, people's life is increasingly tied to network and electronic products with various functions. With improvement of living standard, tablet computers, smart phones and other portable electronic products are popular, and wearable intelligent electronic products which are more portable are also rapidly developed.

Currently, the electronic device is usually provided with sensors, so that the electronic device can respond to a user's operation on the electronic device, thus achieving intelligent human-computer interaction.

For obtaining a direction, the user may take an image of nearby objects by using the electronic device and acquire the direction by searching contents displayed in the image; or the user may start dedicated mapping software and acquire the direction by the dedicated mapping software.

In view of the above, the way for obtaining the direction by the electronic device is complicated.

SUMMARY

The disclosure provides an information processing method. The information processing method includes: obtaining first parameter information indicating a current posture of a first body part by a first sensor among M sensors of an electronic device fixed on the first body part; judging whether the first parameter information meets a predetermined condition; determining that the current posture of the first body part is a first posture in a case that the first parameter information meets the predetermined condition; obtaining N second parameters by N sensors other than the first sensor among the M sensors, wherein 1≤N<M; and determining a first posture direction that the first body part in the first posture points towards based on the N second parameters.

The disclosure further provides an electronic device. The electronic device includes: a first obtaining module configured to obtain first parameter information indicating a current posture of a first body part by a first sensor among M sensors of the electronic device fixed on the first body part; a judging module configured to judge whether the first parameter information meets a predetermined condition; a first determining module configured to determine that the current posture of the first body part is a first posture in a case that the first parameter information meets the predetermined condition; a second obtaining module configured to obtain N second parameters by N sensors other than the first sensor among the M sensors, wherein 1≤N<M; and a second determining module configured to determine a first posture direction that the first body part in the first posture points towards based on the N second parameters.

The disclosure further provides an information processing method. The information processing method includes: obtaining first parameter information indicating a first posture of a first body part by a first sensor; judging whether the first parameter information meets a predetermined condition; obtaining second parameter information indicating a first direction of the first body part by a second sensor in a case that the first parameter information meets the predetermined condition; and determining a first posture direction that the first body part in the first posture points towards based on the first parameter information and the second parameter information.

DETAILED DESCRIPTION OF THE EMBODIMENTS

With the information processing method and the electronic device, a direction can be obtained simply.

It is provided an information processing method applicable to an electronic device. The method includes:

obtaining first parameter information indicating a current posture of a first body part by a first sensor among M sensors of the electronic device fixed on the first body part;

judging whether the first parameter information meets a predetermined condition;

determining that the current posture of the first body part is a first posture in a case that the first parameter meets the predetermined condition;

obtaining N second parameters by N sensors other than the first sensor among the M sensors, where 1≤N<M; and determining a first posture direction that the first body part in the first posture points towards based on the N second parameters.

It can be seen from the above that, the first parameter information indicating the current posture of the first body part is obtained by the first sensor in a case that the electronic device is fixed on the first body part of the user; and after it is determined based on the first parameter information that the current posture is the first posture, the first posture direction which is a direction that the first body part points towards is obtained by other sensors. In this way, the direction can be obtained simply by the electronic device.

For better understanding, the above-described technical solutions are described in detail below in conjunction with the drawings and the embodiments.

First Embodiment

The first embodiment provides an information processing method applicable to an electronic device. The electronic device includes a frame and M sensors fixed on the frame, where M is a positive integer greater than 1. The frame includes a fixing component through which the electronic device is capable of being fixed on a first body part of a user. In practice, the electronic device may be a smart watch, an intelligent bracelet, an intelligent glass or a smart glove, which is not limited herein.

Figure 1:
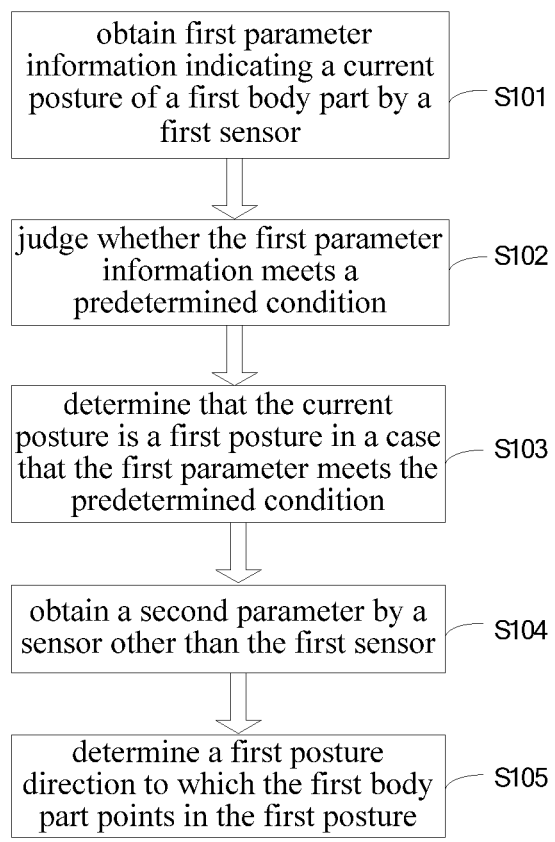
FIG. 1 is a flowchart of an information processing method according to a first embodiment of the present application.

Reference is made to FIG. 1, which is a flowchart of an information processing method according to the first embodiment of the present application. The method includes following Steps 101 to 105.

Step 101 may include, obtaining first parameter information indicating a current posture of the first body part by a first sensor among the M sensors of the electronic device fixed on the first body part.

Step 102 may include, judging whether the first parameter information meets a predetermined condition.

Step 103 may include, determining that the current posture of the first body part is a first posture in a case that the first parameter meets the predetermined condition.

Step 104 may include, obtaining N second parameters by N sensors other than the first sensor among the M sensors, where 1≤N<M.

Step 105 may include, determining a first posture direction that the first body part in the first posture points towards based on the N second parameters.

In an implementation, the first posture direction is a direction in a geodetic reference system.

In an implementation, the first posture is a pointing posture.

In an implementation, the fixing component may be a part of the frame.

For example, in a case that the electronic device is a smart watch, the fixing component is a watchband of the smart watch for fixing the smart watch on a wrist of the user; and in a case that the electronic device is an intelligent glass, the fixing component is a spectacle frame of the intelligent glass for fixing the intelligent glass on a head of the user.

The fixing component may also be the entire frame.

For example, in a case that the electronic device is an intelligent bracelet, the fixing component is the entire ring frame of the intelligent bracelet for fixing the intelligent bracelet on a wrist of the user; and in a case that the electronic device is a smart glove, the fixing component is the entire hand-like structure of the smart glove for fixing the smart gloves on a hand of the user.

In an implementation, the first posture direction is a direction in a geodetic reference system, and the geodetic reference system is a geographic coordinate system consisting of latitude and longitude coordinates.

The solution of the embodiment is described from a perspective of human-computer interaction by taking a smart watch worn on left hand of a user A as an example.

For example, the user A wants to acquire a front direction.

The user A firstly raises the left first toward the front, and then stretches out the index finger of the left hand to make the smart watch perform steps 101-103, for acquiring the first parameter information indicating the current posture of the left hand of the user A by the first sensor and determining that the current posture of the left hand of the user A is a first posture based on the first parameter information.

The smart watch then performs steps 104-105, for acquiring a second parameter of a direction that the index finger of the left hand of the user A points towards by sensors other than the first sensor and determining that the direction that the index finger of the left hand of the user A points towards is 35 degrees north by east based on the second parameter.

Content of "35 degrees north by east" is displayed on the smart watch to help the user A to acquire the front direction.

After preliminarily describing the information processing method provided by the present embodiment by the above-mentioned example, the information processing method will be described below in details in following two aspects: determination of the first posture direction and application of the first posture direction.

In the first aspect, the determination of the first posture direction is as follows.

Firstly, in step 101, first parameter information is obtained by a first sensor among the M sensors in a case that the electronic device is fixed on the first body part through the fixing component, where the first parameter information indicates a current posture of the first body part.

In an implementation, the first sensor may be arranged based on the first body part corresponding to the electronic device, the fixing component of the electronic device and the first posture to be determined.

For example, in a case that the electronic device is a smart watch, the corresponding first body part is a wrist of a user, and the fixing component of the electronic device is a watchband pressing the wrist.

Figure 2:
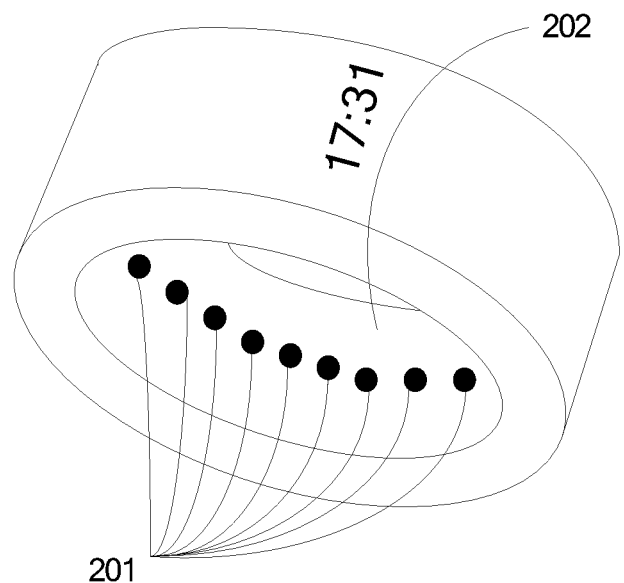
FIG. 2 is a schematic diagram of arrangement of a first sensor in a case that the electronic device is a smart watch according to the first embodiment of the present application.

Reference is made to FIG. 2, which is a schematic diagram of arrangement of a first sensor according to the first embodiment of the present application, where the electronic device is a smart watch. As shown in FIG. 2, if the first posture to be determined is a posture of a finger, the first sensor 201 is implemented as an array of pressure sensors distributed on a first surface 202 of the watch pressing the wrist. Each of the pressure sensors in the array of the pressure sensors senses a pressure applied on the watchband by the wrist muscle and records a state of wrist muscle where the pressure sensor is located. Since different states of wrist muscle correspond to different postures of the finger, the smart watch can obtain the first parameter information indicating the current posture of the finger by the array of the pressure sensors.

If the first posture to be determined is merely a posture of raising the arm, the first sensor may be implemented as an acceleration transducer. The acceleration transducer can record a moving track of the electronic device along a direction opposite to the direction of the gravity when the user raises his hand and points towards the front. In this way, the smart watch can obtain the first parameter information indicating an arm raising posture by the acceleration transducer.

In a case that the electronic device is a smart glove, the corresponding first body part is a hand of the user, and the fixing component is the entire hand-like structure. In this case, the first sensor may be implemented as a set of range sensors. The set of range sensors may be respectively disposed in an area of the smart glove close to the wrist and an area of the smart glove close to each fingertip. Each of the range sensors in the set of the range sensors records a distance between itself and other range sensors. Therefore, the smart glove can obtain the first parameter information indicating the current posture of the hand by the set of the range sensors.

In an implementation, the first sensor may also be implemented as an image sensor, and the first parameter information is a first image of the first body part obtained by the image sensor.

After the first parameter information is obtained in step 101, steps 102 and 103 are performed for determining whether the first parameter information meets a predetermined condition and determining that the current posture of the first body part is a first posture in a case that the first parameter information meets the predetermined condition, where the first posture is a pointing posture.

In an implementation, the predetermined condition corresponds to the first posture to be determined.

The smart watch is taken as an example. In a case that the first posture to be determined is a posture of stretching out a finger and the first sensor is the array of the pressure sensors which is distributed on the surface of the watch pressing the wrist, the first parameter information is a pressure value received by each of the pressure sensors in the array of the pressure sensors. A first value range of the pressure value received by each of the pressure sensors in the array of the pressure sensors when a finger is stretched out is stored in advance in the smart watch. In this case, the predetermined condition is that the first parameter information falls within the first value range.

After it is determined that the current posture of the first body part is the first posture in step 103, step 104 and step 105 are performed, for obtaining N second parameters by N sensors other than the first sensor among the M sensors, where 1≤N≤M; and determining a first posture direction that the first body part in the first posture points towards based on the N second parameters.

In an implementation, the N sensors may be gyroscope sensors. A three-dimensional coordinate space is defined by the gyroscope sensors in a case that the N sensors are gyroscope sensors. A direction of a pointer in the three-dimensional coordinate space is recorded in the electronic device in advance, and the direction of the pointer may be any one of due east, due west, due south and due north. A relative angle between the first posture direction and a reference direction of the electronic device is recorded in the electronic device in advance. After it is determined that the current posture of the first body part is the first posture, the gyroscope sensors acquire a heeling condition of the electronic device in the three-dimensional coordinate space and the electronic device acquires the first posture direction that the first body part points towards based on the heeling condition, the direction of the pointer and the relative angle.

Figure 3:
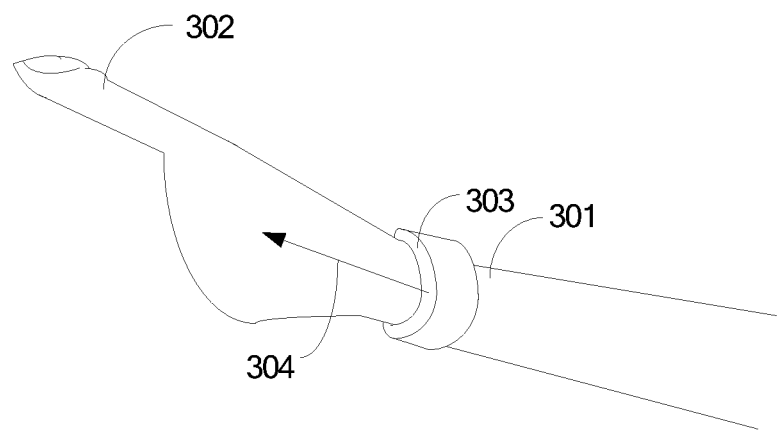
FIG. 3 is a schematic diagram of a reference direction of an electronic device according to the first embodiment of the present application.

In an implementation, as shown in FIG. 3, the electronic device is a smart watch. Since when the smart watch is worn on the wrist 301 of the user, a normal direction 304 of a lateral surface 303 of the smart watch close to a finger 302 is almost the same as the direction that the finger 302 points towards, the normal direction 304 of the lateral surface 303 is set as the reference direction of the electronic device, and the relative angle between the first posture direction and the reference direction of the electronic device is stored as 0 degree.

Figure 4:
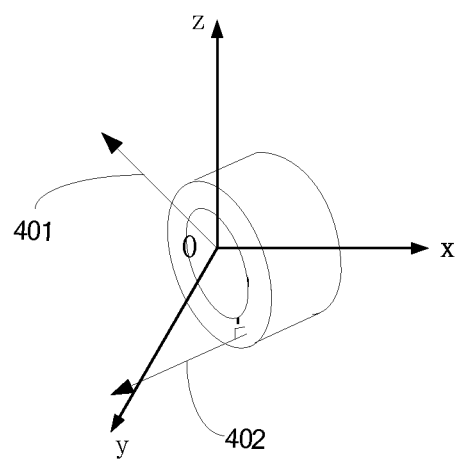
FIG. 4 is a schematic diagram of a first posture direction obtained by a gyroscope sensor according to the first embodiment of the present application.

Reference is made to FIG. 4, which is a schematic diagram of the first posture direction obtained by the gyroscope sensor according to the first embodiment of the present application. As shown in FIG. 4, the electronic device is a smart watch, a direction of due north 401 is stored in advance in a three-dimensional coordinate space including x-axis, y-axis and z-axis which is defined by the gyroscope sensor.

After the current posture of the first body part is determined as the first posture, the gyroscope sensor determines the heeling condition of the first electronic device in the three-dimensional coordinate space.

A reference direction 402 of the electronic device is acquired based on the heeling condition. Provided that the relative angle between the first posture direction and the reference direction is 0 degree, that is, the reference direction is the first posture direction, then the first posture direction is calculated based on the relative angle between the due north 401 and the reference direction 402 in a horizontal plane. For example, if a projection direction of the due north 401 on the horizontal plane reaches a projection direction of the reference direction 402 on the horizontal plane after being rotated by 40 degrees clockwise, the orientation of the reference direction 402 is determined as 40 degrees north by east, and then the first posture direction is determined as 40 degrees north by east.

In a second aspect, the application of the first posture direction is as follows.

In the embodiment according to the present application, the method may further include outputting prompt information corresponding to the first posture direction after the first posture direction is determined based on the N second parameters.

In an implementation, the outputting the prompt information corresponding to the first posture direction may include displaying the prompt information on a display unit of the electronic device or playing the prompt information by a voice unit, which is not limited herein.

In an implementation, the prompt information may be direction information such as east, south, west and north, or may be information which is acquired from a database based on the direction information.

A way for acquiring the prompt information from the database based on the direction information will be explained in detail as follows.

In a case that at least one of the N sensors is the first position sensor configured to obtain the current position of the electronic device, outputting the prompt information corresponding to the first posture direction includes:

invoking a first database;

determining a virtual target object from the first database based on the first posture direction and the current position, where the virtual target object corresponds to a first object, and the first object is an object which is in the first posture direction with the current position as a starting point;

obtaining target information of the virtual target object stored in advance, and setting the target information as the prompt information; and outputting the prompt information.

In an implementation, the first position sensor may be GPS and other positioning sensors. The first database is a database which is stored in the electronic device in advance or stored in other electronic device connected to the electronic device. The geodetic reference system, a coordinates of each of the multiple virtual objects in the geodetic reference system and information corresponding to each of the multiple virtual objects are stored in the first database in advance. The electronic device can obtain coordinates of a current position of the electronic device in the geodetic reference system via the first position sensor, and determine a virtual target object which is in the first posture direction with coordinates of the current position as a starting point in the geodetic reference system in the first database.

For example, the user A is to determine group buying information of a cafe nearby.

The user A firstly raises his left hand on which a smart watch is worn and stretches out the index finger to point to the cafe, and the smart watch determines that the cafe is in the due south direction of the user A.

A GPS positioning sensor in the smart watch then acquires coordinates of the current position of the user A in the geodetic reference system, which is 40 degrees north latitude and 116 degrees east longitude.

The smart watch then invokes the first database of a server, determines a cafe which is in the due south direction with 40 degrees north latitude and 116 degrees east longitude as a starting point stored in the database as the virtual target object, and obtains the group buying information of the cafe stored in advance.

The group buying information of the cafe is displayed on the display of the smart watch and the user A can know the group buying information.

The current position of the electronic device is obtained by the first position sensor, and the information of the virtual object which is in the first posture direction with the current position as a starting point in the geodetic reference system is obtained from the database based on the current position and the first posture direction. Therefore, the information of the objects around the electronic device can be obtained by the electronic device simply.

In an implementation, since the number of virtual objects stored in the first database is usually large, there may be multiple virtual objects which are in the first posture direction with the current position as a starting point in the geodetic reference system, and a virtual target object may be determined from the multiple virtual objects by a distance or by a user, the details are as follows.

In a first way, the virtual target object is determined from the multiple virtual objects by a distance.

Determining the virtual target object from the first database based on the first posture direction and the current position includes:

determining K virtual objects from the first database based on the first posture direction and the current position, where the K virtual objects correspond to K first objects, and each of the K first objects is an object which is in the first posture direction with the current position as a starting point; and determining a virtual target object from the K virtual objects, where the virtual target object corresponds to a first target object, and the first target object is an object closest to current position among the K first objects.

Figure 5:
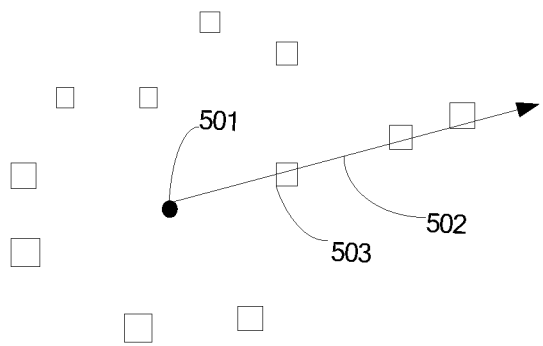
FIG. 5 is a schematic diagram of determining a virtual target object based on a distance according to the first embodiment of the present application.

As shown in FIG. 5, in a case that there are K virtual objects which are in the first posture direction 502 with the current position 501 as a starting point in the geodetic reference system stored in the first database, a distance between the position of each of the K virtual objects and the current position is calculated based on the current position and the position information of the K virtual objects stored in advance, and a virtual object 503 closest to the current position is selected as the virtual target object.

In a second way, the virtual target object is determined from the multiple virtual objects by a user.

Determining the virtual target object from the first database based on the first posture direction and the current position includes:

determining K virtual objects from the first database based on the first posture direction and the current position, where the K virtual objects correspond to K first objects, and each of the K first objects is an object which is in the first posture direction with the current position as a starting point;

displaying K virtual object names respectively corresponding to the K virtual objects;

receiving a selecting operation of selecting a first virtual object name from the K virtual objects names; and determining a virtual object corresponding to the first virtual object name as the virtual target object based on the selecting operation.

For example, a user A is to determine group buying information of a cafe nearby.

The user A firstly raises his left hand on which a smart watch is worn and stretches out the index finger to point to the cafe, and the smart watch determines that the cafe is in a due south direction of the user A.

A GPS positioning sensor in the smart watch then acquires coordinates of the current position where the user A is located in the geodetic reference system, which is 40 degrees north latitude and 116 degrees east longitude.

The smart watch then invokes the first database of a server, determines that there are three virtual objects in the direction of due south with 40 degrees north latitude and 116 degrees east longitude as a starting point stored in the database. Names of the three virtual objects are displayed on the smart watch, which are respectively a cafe, a noodle shop and a bookstore.

The user A then clicks an area in which the cafe is displayed on the display unit of the smart watch such that the smart watch determines the cafe as the virtual target object based on the click operation of the user A and obtains the group buying information of the cafe stored in advance.

The group buying information of the cafe is then displayed on the display of the smart watch such that the user A can know the group buying information.

Another embodiment of the present disclosure provides an electronic device corresponding to the method of the first embodiment of the present application based on the same conception, which is described in the second embodiment in details.

Second Embodiment

The second embodiment provides an electronic device including a frame and M sensors fixed on the frame, where M is a positive integer greater than 1. The frame includes a fixing component through which the electronic device is capable of being fixed on a first body part of a user. In practice, the electronic device may be a smart watch, an intelligent bracelet, an intelligent glass, a smart glove or other electronic devices, which is not limited herein.

Figure 6:
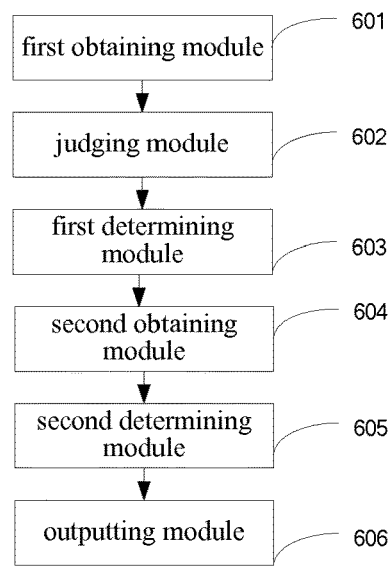
FIG. 6 is a structural diagram of an electronic device according to a second embodiment of the present application.

Reference is made to FIG. 6, which is a structural diagram of the electronic device according to the second embodiment of the present application. The electronic device further includes a first obtaining module 601, a judging module 602, a first determining module 603, a second obtaining module 604 and a second determining module 605.

The first obtaining module 601 is configured to obtain first parameter information indicating a current posture of the first body part by a first sensor among the M sensors of the electronic device fixed on the first body part.

The judging module 602 is configured to judge whether the first parameter information meets a predetermined condition.

The first determining module 603 is configured to determine that the current posture of the first body part is a first posture in a case that the first parameter meets the predetermined condition.

The second obtaining module 604 is configured to obtain N second parameters by N sensors other than the first sensor among the M sensors, where $1 \leq N < M$.

The determining module 605 is configured to determine a first posture direction that the first body part in the first posture points towards based on the N second parameters.

In the present embodiment, the electronic device may further include an outputting module 606 configured to output prompt information corresponding to the first posture direction based on the first posture direction.

In the present embodiment, in a case that at least one of the N sensors is a first position sensor configured to obtain a current position of the electronic device, the outputting module 606 includes:

an invoking unit configured to invoke a first database;

a determining unit configured to determine a virtual target object from the first database based on the first posture direction and the current position, where the virtual target object corresponds to a first object, and the first object is an object which is in the first posture direction with the current position as a starting point;

an obtaining unit configured to obtain target information of the virtual target object stored in advance and take the target information as prompt information; and an outputting unit configured to output the prompt information.

In an implementation, the determining unit is further configured to:

determine K virtual objects from the first database based on the first posture direction and the current position, where the K virtual objects correspond to K first objects, and each of the K first objects is an object which is in the first posture direction with the current position as a starting point; and determine a virtual target object from the K virtual objects, where the virtual target object corresponds to a first target object, and the first target object is an object closest to the current position among the K first objects.

In an implementation, the determining unit is further configured to:

determine K virtual objects from the first database based on the first posture direction and the current position, where the K virtual objects correspond to the K first objects, and each of the K first objects is an object which is in the first posture direction with the current position as a starting point;

display K virtual object names respectively corresponding to the K virtual objects;

receive a selecting operation of selecting a first virtual object name from the K virtual objects names; and determine a virtual object corresponding to the first virtual object name as the virtual target object based on the selecting operation.

The electronic device of the present embodiment and the information processing method of the first embodiment are based on the same inventive concept. Since the processes of the method are described above in detail, the structure and implementation of the electronic device of the present embodiment can be obtained by those skilled in the art based on the above description, which will not be described in detail herein.

Third Embodiment

The third embodiment provides an information processing method applicable to an electronic device. The electronic device includes a frame and M sensors fixed on the frame, where M is a positive integer greater than 1. The frame includes a fixing component through which the electronic device is capable of being fixed on a first body part of a user. In practice, the electronic device may be a smart watch, an intelligent bracelet, an intelligent glass or a smart glove, which is not limited herein.

Figure 7:
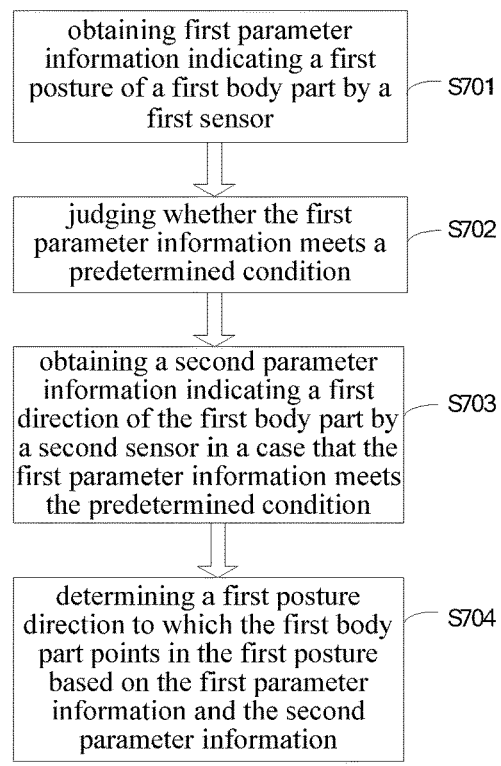
FIG. 7 is a flowchart of an information processing method according to a third embodiment of the present application.

Reference is made to FIG. 7, which is a flowchart of an information processing method according to the third embodiment of the present application. The method includes following Steps 701 to 704.

Step 701 may include, obtaining first parameter information indicating a first posture of the first body part by a first sensor.

Step 702 may include, judging whether the first parameter information meets a predetermined condition;

Step 703 may include, obtaining a second parameter information indicating a first direction of the first body part by a second sensor in a case that the first parameter information meets the predetermined condition; and Step 704 may include, determining a first posture direction that the first body part in the first posture points towards based on the first parameter information and the second parameter information.

The method may further include: outputting prompt information corresponding to the first posture direction.

In an implementation, outputting prompt information corresponding to the first posture direction may include: invoking a first database; determining a virtual target object corresponding to a first target object that the first body part points to in the first posture direction; obtaining target information of the virtual target object pre-stored in the first database; and outputting the target information as the prompt information.

In an implementation, determining a virtual target object corresponding to a first target object that the first body part points to in the first posture direction may include: determining k virtual objects respectively corresponding to k first objects that the first body part points to in the first posture direction; determining a closest first object with respect to the first body part from the k first objects as the first target object; and determining the virtual target objects from the k virtual objects corresponding to the closest first object.

In an implementation, determining a virtual target object corresponding to a first target object that the first body part points to in the first posture direction may include: determining K virtual objects respectively corresponding to K first objects that the first body part points to in the first posture direction; displaying K virtual object names respectively corresponding to the K virtual objects; receiving a selecting operation of selecting a first virtual object name from the K virtual objects names; and determining a virtual object corresponding to the first virtual object name as the virtual target object based on the selecting operation.

In an implementation, the first posture is a pointing posture.

The information processing method of the present embodiment and the information processing method of the first embodiment are based on the same inventive concept. Since the processes of the method are described above in detail, the implementation of the electronic device of the present embodiment can be obtained by those skilled in the art based on the above description, which will not be described in detail herein.

With the method and the electronic device provided in the embodiments of the present application, the first parameter information indicating the current posture of the first body part is obtained by the first sensor in a case that the electronic device is fixed on the first body part of the user; and after the current posture is determined as the first posture based on the first parameter information, a first posture direction that the first body part points towards is obtained by other sensors. Therefore, the first posture direction can be obtained simply by the electronic device.

In addition, with the method and the electronic device provided in the embodiments of the present application, the current position of the electronic device is obtained by the first position sensor, and the information of an object which is in the first posture direction with the current position as a starting point is obtained from the database based on the current position and the first posture direction. Therefore, the information of the object around the electronic device can be obtained by the electronic device simply.

Those skilled in the art can understand that the embodiment of the present disclosure may be implemented as a method, a system or a computer program product. Therefore, the present disclosure may be implemented as an entire hardware embodiment, an entire software embodiment or an embodiment of both software and hardware. In addition, the present disclosure may be in a form of a computer program product which is implemented on one or more computer usable storage medium (including but not limited to a disk storage, a CD-ROM, and an optical memory, etc.) containing computer usable program codes.

The present disclosure is described with reference to the flowcharts and/or block diagrams of the method, the device (system), and the computer program product according to the embodiments of the present disclosure. It should be understood that each process and/or block of the flowcharts and/or block diagrams and the combination of the process and/or block of the flowcharts and/or block diagrams may be achieved by a computer program instruction. These computer program instructions may be provided to a processor of a general purpose computer, special purpose computer, embedded processor or other programmable data processing apparatus to produce a machine such that the instructions executed by the processor of the computer or other programmable data processing apparatus produce an apparatus which is used to realize a specified function in one or more processes of the flowcharts and/or one or more blocks of the block diagrams.

These computer program instructions may also be stored in a computer-readable memory that can direct the computer or the other programmable data processing apparatus to operate in a specific manner, such that the instructions stored in the computer-readable memory may produce an article including an instruction means. The instruction means is used to achieve the function specified in the one or more processes of the flowcharts and/or the one or more blocks of the block diagrams.

These computer program instructions may also be loaded into the computer or the other programmable data processing apparatus so as to perform a series of operation steps on the computer or the other programmable apparatus to produce a computer-processing. Hence, the instructions which are executed on the computer or the other programmable apparatus are used to realize the steps for realizing the function specified in the one or more processes of the flowcharts and/or the one or more blocks of the block diagrams.

The computer program instructions corresponding to the two information processing methods according to the embodiments of the present application may be stored in a storage medium such as a compact disk, a hard disk or a flash memory disk.

Once the computer program instructions corresponding to the information processing method in the storage medium is read or executed by an electronic device, the information processing method includes the following steps:

obtaining first parameter information by a first sensor among the M sensors in a case that the electronic device is fixed on the first body part through the fixing component, where the first parameter information indicates a current posture of the first body part;

judging whether the first parameter information meets a predetermined condition;

determining that the current posture of the first body part is a first posture in a case that the first parameter meets the predetermined condition, where the first posture is a pointing posture;

obtaining N second parameters by N sensors other than the first sensor among the M sensors, where $1 \leq N < M$; and determining a first posture direction that the first body part points towards based on the N second parameters, where the first posture direction is a first posture direction that the first body part being in the first posture points towards.

Optically, other computer instructions are also stored in the storage medium, and these computer instructions are executed after the computer instructions corresponding to the step of determining the first posture direction that the first body part points towards based on the N second parameters, and these computer instructions, when being executed, perform the following steps:

outputting prompt information corresponding to the first posture direction.

Optically, in a case that at least one of the N sensors is a first position sensor configured to obtain the current position of the electronic device, the computer instructions stored in the storage medium corresponding to the step of outputting prompt information corresponding to the first posture direction, when being executed, perform the following steps:

invoking a first database;

determining a virtual target object from the first database based on the first posture direction and the current position, where the virtual target object corresponds to a first object, and the first object is an object which is in the first posture direction with the current position as a starting point;

obtaining target information of the virtual target object stored in advance, and taking the target information as the prompt information; and outputting the prompt information.

Optically, the computer instructions stored in the storage medium corresponding to the step of the determining a virtual target object from the first database based on the first posture direction and the current position, when being executed, perform the following steps:

determining K virtual objects from the first database based on the first posture direction and the current position, where the K virtual objects correspond to K first objects, and each of the K first objects is an object which is in the first posture direction with the current position as a starting point; and determining a virtual target object from the K virtual objects, where the virtual target object corresponds to a first target object, and the first target object is an object closest to the current position among the K first objects.

Optically, the computer instructions stored in the storage medium corresponding to the step of the determining a virtual target object from the first database based on the first posture direction and the current position, when being executed, perform the following steps:

determining K virtual objects from the first database based on the first posture direction and the current position, where the K virtual objects correspond to the K first objects, and each of the K first objects is an object which is in the first posture direction with the current position as a starting point;

displaying K virtual object names corresponding to the K virtual objects;

receiving a selecting operation of selecting a first virtual object name from the K virtual objects names; and determining a virtual object corresponding to the first virtual object name as the virtual target object based on the selecting operation.

Although the preferred embodiments according to the present disclosure has been described, other changes and modifications can be made to these embodiments by the skilled in the art based on the basic inventive concept. Therefore, the appended claims are explained as inclusive of the preferred embodiments and all the changes and modifications falling within the scope of the present disclosure.

It is obvious that various changes and variations may be made by the skilled in the art without departing from the spirit and the scope of the present disclosure. Hence, the present invention intends to contain these changes and variations which fall within the scope of the claims and the equivalent technology of the present disclosure.

What is claimed is:

1. An information processing method comprising:
obtaining, by a first sensor among M sensors of a wearable electronic device, first parameter information indicating a current posture of a first human body part, wherein
the wearable electronic device comprises a frame,
the M sensors are fixed on the frame, and
the M sensors are fixed on the first human body part of a user through the frame;
judging, by the wearable electronic device, whether the first parameter information meets a predetermined condition;
determining, by the wearable electronic device, that the current posture of the first human body part is a first posture in a case that the first parameter information meets the predetermined condition;
obtaining N second parameters by N sensors other than the first sensor among the M sensors in a case that the current posture of the first human body part is determined as the first posture, wherein
$1 \leq N < M$,
wherein the N sensors comprises a plurality of gyroscope sensors and a GPS positioning sensor, and
wherein the GPS positioning sensor acquires coordinates of a position of a user using the wearable electronic device in a geodetic reference system;
determining, by the wearable electronic device based on parameters of the N second parameters obtained by the plurality of gyroscope sensors, a relative angle of a first posture direction relative to due north in a horizontal plane in the geodetic reference system, wherein the first posture direction is a direction that the first human body part in the first posture points towards; and
outputting prompt information corresponding to the relative angle of the first posture direction and the coordinates of the position of the user,
wherein the outputting prompt information corresponding to the relative angle of the first posture direction comprises at least one of:
displaying, by a displaying unit of the wearable electronic device, the prompt information; and
playing, by a voice unit of the wearable electronic device, the prompt information.

2. The method according to claim 1 wherein the outputting prompt information corresponding to the relative angle of the first posture direction comprises:
invoking a first database, wherein the first database stores the geodetic reference system, coordinates of each virtual target object in the geodetic reference system, and information corresponding to each virtual target object;
determining a virtual target object from the first database based on the relative angle of the first posture direction relative to due north and the coordinates of the position of the user, wherein the virtual target object corresponds to a first object, and the first object is an object which is in the first posture direction with the position of the user as a starting point;
obtaining target information of the virtual target object stored in advance, and taking the target information as the prompt information; and
outputting the prompt information.

3. The method according to claim 2, wherein determining the virtual target object from the first database based on the first posture direction and the coordinates of the position of the user comprises:
determining K virtual objects from the first database based on the relative angle of the first posture direction relative to due north and the coordinates of the position of the user, wherein the K virtual objects correspond to K first objects, and each of the K first objects is an object which is in the first posture direction with the position of the user as a starting point; and
determining the virtual target object from the K virtual objects, wherein the virtual target object corresponds to a first target object, and the first target object is an object closest to the position of the user among the K first objects.

4. The method according to claim 2, wherein determining the virtual target object from the first database based on the relative angle of the first posture direction relative to due north and the coordinates of the position of the user comprises:
determining K virtual objects from the first database based on the relative angle of the first posture direction relative to due north and the coordinates of the position of the user, wherein the K virtual objects correspond to K first objects, and each of the K first objects is an object which is in the first posture direction with the position of the user as a starting point;
displaying K virtual object names respectively corresponding to the K virtual objects;
receiving a selecting operation of selecting a first virtual object name from the K virtual objects names; and
determining a virtual object corresponding to the first virtual object name as the virtual target object based on the selecting operation.

5. The method according to claim 1, wherein the first posture is a pointing posture.

6. A wearable electronic device, the wearable electronic device having a frame and M sensors fixed on the frame, the M sensors being fixed on a first human body part of a user through the frame, the wearable electronic device comprising a processor and a non-transitory memory storing instructions that, when executed by the processor, cause the processor to:
obtain first parameter information indicating a current posture of the first human body part by a first sensor among the M sensors of the wearable electronic device;
judge whether the first parameter information meets a predetermined condition;
determine that the current posture of the first human body part is a first posture in a case that the first parameter information meets the predetermined condition;

obtain N second parameters by N sensors other than the first sensor among the M sensors in a case that the current posture of the first human body part is determined as the first posture, wherein
1≤N<M, and
wherein the N sensors comprises a plurality of gyroscope sensors and a GPS positioning sensor; wherein the GPS positioning sensor acquires coordinates of a position of a user using the wearable electronic device in a geodetic reference system;
determine a relative angle of a first posture direction relative to due north in a horizontal plane in the geodetic reference system; wherein the first posture direction is a direction that the first human body part in the first posture points towards; and
output prompt information corresponding to the relative angle of the first posture direction and the coordinates of the position of the user,
wherein the prompt information corresponding to the relative angle of the first posture direction is outputted by at least one of the following:
displaying, by a displaying unit of the wearable electronic device, the prompt information; and
playing, by a voice unit of the wearable electronic device, the prompt information.

7. The wearable electronic device according to claim 6 wherein the instructions, when executed by the processor, further cause the processor to:
invoke a first database, wherein the first database stores the geodetic reference system, coordinates of each virtual target object in the geodetic reference system and information corresponding to each virtual target object;
determine a virtual target object from the first database based on the relative angle of the first posture direction relative to due north and the coordinates of the position of the user, wherein the virtual target object corresponds to a first object, and the first object is an object which is in the first posture direction with the position of the user as a starting point;
obtain target information of the virtual target object stored in advance and take the target information as the prompt information; and
output the prompt information.

8. The wearable electronic device according to claim 7, wherein the instructions, when executed by the processor, further cause the processor to:
determine K virtual objects from the first database based on the relative angle of the first posture direction relative to due north and the coordinates of the position of the user, wherein the K virtual objects correspond to K first objects, and each of the K first objects is an object which is in the first posture direction with the position of the user as a starting point; and
determine the virtual target object from the K virtual objects, wherein the virtual target object corresponds to a first target object, and the first target object is an object closest to the position of the user among the K first objects.

9. The wearable electronic device according to claim 7, wherein the instructions, when executed by the processor, further cause the processor to:
determine K virtual objects from the first database based on the relative angle of the first posture direction relative to due north and the coordinates of the position of the user, wherein the K virtual objects correspond to K first objects, and each of the K first objects is an object which is in the first posture direction with the position of the user as a starting point;
display K virtual object names respectively corresponding to the K virtual objects;
receive a selecting operation of selecting a first virtual object name from the K virtual object names; and
determine a virtual object corresponding to the first virtual object name as the virtual target object based on the selecting operation.

10. The wearable electronic device according to claim 6, wherein the first posture is a pointing posture.

* * * * *